US00PP17586P2

(12) United States Plant Patent
Hofmann

(10) Patent No.: US PP17,586 P2
(45) Date of Patent: Apr. 10, 2007

(54) **NEW GUINEA *IMPATIENS* PLANT NAMED 'FISCO DEEPSALM'**

(50) Latin Name: *Impatiens hawkeri*
Varietal Denomination: Fisco Deepsalm

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 11/241,395

(22) Filed: Sep. 30, 2005

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of New Guinea *Impatiens* plant named 'Fisco Deepsalm', characterized by its relatively compact, outwardly spreading and uniformly mounded plant habit; rounded growth habit; freely branching and freely flowering habit; large medium green-colored foliage; large salmon orange-colored flowers with red-colored centers; and flowers that are positioned above or beyond the foliage.

1 Drawing Sheet

Botanical designation: *Impatiens hawkeri.*
Cultivar denomination: 'Fisco Deepsalm'.

BACKGROUND OF THE INVENTION

The present Invention relates to a new and distinct cultivar of New Guinea *Impatiens* plant, botanically known as *Impatiens hawkeri,* and hereinafter referred to by the name 'Fisco Deepsalm'.

The new *Impatiens* is a product of a planned breeding program conducted by the Inventor in Hillscheid, Germany and Galdar, Canary Islands, Spain. The objective of the breeding program is to develop new compact *Impatiens* cultivars that flower relatively early and have attractive flower coloration.

The new *Impatiens* originated from a cross-pollination made by the Inventor during the summer of 2000 in Hillscheid, Germany of the *Impatiens hawkeri* cultivar Kimali, disclosed in U.S. Plant Pat. No. 14,033, as the female, or seed, parent with a proprietary selection of *Impatiens hawkeri* identified as code number K00-7176-1, not patented, as the male, or pollen, parent. The cultivar Fisco Deepsalm was discovered and selected by the Inventor as a flowering plant within the progeny of the stated cross-pollination in a controlled environment in Galdar, Canary Islands, Spain in April, 2001.

Asexual reproduction of the new cultivar by terminal cuttings in Galdar, Canary Islands, Spain since September, 2001, has shown that the unique features of this new *Impatiens* are stable and reproduced true to type in successive generations.

SUMMARY OF THE INVENTION

The following traits have been repeatedly observed and are determined to be the unique characteristics of 'Fisco Deepsalm'. These characteristics in combination distinguish 'Fisco Deepsalm' as a new and distinct *Impatiens* cultivar:

1. Relatively compact, outwardly spreading and uniformly mounded plant habit; rounded growth habit.
2. Freely branching and freely flowering habit.

3. Large medium green-colored foliage.
4. Large salmon orange-colored flowers with red-colored centers.
5. Flowers that are positioned above or beyond the foliage.

Plants of the new *Impatiens* can be compared to plants of the female parent, the cultivar Kimali. In side-by-side comparisons conducted by the Inventor in Hillscheid, Germany, plants of the new *Impatiens* differed from plants of the cultivar Kimali in the following characteristics:

1. Plants of the new *Impatiens* were shorter than plants of the cultivar Kimali.
2. Plants of the new *Impatiens* had slightly smaller flowers than plants of the cultivar Kimali.
3. Plants of the new *Impatiens* and the cultivar Kimali differed in flower color.

Plants of the new *Impatiens* can be compared to plants of the male parent selection. In side-by-side comparisons conducted by the Inventor in Hillscheid, Germany, plants of the new *Impatiens* differed from plants of the male parent selection in the following characteristics:

1. Plants of the new *Impatiens* had larger flowers than plants of the male parent selection.
2. Plants of the new *Impatiens* and the male parent selection differed in flower color.

Plants of the new *Impatiens* can also be compared to plants of the cultivar Fisnics Dark Salmon, disclosed in U.S. Plant Pat. No. 13,232. In side-by-side comparisons conducted by the Inventor in Hillscheid, Germany, plants of the new *Impatiens* differed from plants of the cultivar Fisnics Dark Salmon in the following characteristics:

1. Plants of the new *Impatiens* were smaller than plants of the cultivar Fisnics Dark Salmon.
2. Plants of the new *Impatiens* had lighter green-colored leaves than plants of the cultivar Fisnics Dark Salmon.
3. Plants of the new *Impatiens* had lighter-colored flowers than plants of the cultivar Fisnics Dark Salmon.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Fisco Deepsalm' grown in a container.

DETAILED BOTANICAL DESCRIPTION

The cultivar Fisco Deepsalm has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers and the aforementioned photograph and following observations and measurements were taken about three months later. During the production of the plants, day temperatures were about 16° C. to 20° C. and night temperatures were about 16° C. In the following description, color references are made to The Royal Horticultural Society Colour Chart, 2001 Edition, except where general terms of ordinary dictionary significance are used.

Botanical classification: *Impatiens hawkeri* cultivar Fisco Deepsalm.

Parentage:

*Female parent.*—*Impatiens hawkeri* cultivar Kimali, disclosed in U.S. Plant Pat. No. 14,033.

*Male parent.*—Proprietary selection of *Impatiens hawkeri* identified as code number K00-7176-1, not patented.

Propagation:

*Type cutting.*—Terminal tip cuttings.

*Time to initiate roots.*—Summer: About 10 days at 24° C. Winter: About 12 to 15 days at 21° C.

*Time to produce a rooted cutting.*—Summer: About 15 days at 24° C. Winter: About 18 to 20 days at 21° C.

*Root description.*—Fine, fibrous; 159A in color.

*Rooting habit.*—Freely branching.

Plant description:

*General appearance.*—Relatively compact, outwardly spreading and uniformly mounded plant growth habit; low and rounded growth habit; freely branching habit; bushy appearance; freely flowering. Low vigor.

*Crop time.*—From a rooted cutting, about nine to ten weeks are required to produce finished flowering plants in 12-cm containers.

*Plant height.*—About 9.7 cm.

*Plant diameter or spread.*—About 19.8 cm.

*Lateral branches.*—Quantity per plant: About six. Length: About 4 cm to 6 cm. Diameter: About 4 mm to 6 mm. Internode length: About 5 mm to 10 mm. Texture: Smooth, glabrous. Color: 185B.

*Foliage description.*—Arrangement: Primarily in whorls. Length: About 11.4 cm. Width: About 4.3 cm. Shape: Elliptic. Apex: Acuminate. Base: Acute. Margin: Serrulate with ciliation. Texture, upper and lower surfaces: Smooth, slightly rugose; glabrous. Color: Developing foliage, upper surface: 137A. Developing foliage, lower surface: 137B. Fully expanded foliage, upper surface: Between, including 137A and 139A. Fully expanded foliage, lower surface: 138B. Venation, upper surface: 185D. Venation, lower surface: 185B. Petiole: Length: About 1.2 cm. Diameter: About 3 mm. Texture, upper and lower surfaces: Smooth, glabrous. Color, upper surface: 185C. Color, lower surface: 185A.

Flower description:

*Flower type and flowering habit.*—Single, large and rounded flowers. Freely and continuously flowering; usually about six to nine flowers and flower buds per lateral branch. Flowers positioned above or beyond the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Early flowering habit; plants begin flowering about nine weeks after planting.

*Flower buds.*—Length: About 2 cm. Diameter: About 1.5 cm. Shape: Ovoid. Color: 52A.

*Flower length.*—About 7 cm.

*Flower width.*—About 6.7 cm.

*Flower depth.*—About 1.2 cm.

*Petals.*—Quantity: Five per flower, imbricate. Length: Banner petals: About 3.3 cm. Lateral and base petals: About 3.4 cm to 3.6 cm. Width: Banner petal: About 5.5 cm. Lateral petals: About 3.2 cm. Base petals: About 3.8 cm. Shape: Cordate. Apex: Moderately lobed; emarginate. Base: Attenuate. Margin: Entire. Aspect: Nearly flat to slightly concave. Texture, upper and lower surfaces: Smooth; satiny. Color: When opening, upper surface: 40A. When opening, lower surface: 52A. Fully opened, upper surface: 40C to 40D overlain with 43B; towards the base, 46B; color becoming closer to 32C with development. Fully opened, lower surface: 52B.

*Spur.*—Quantity: One per flower. Length: About 6.5 cm. Diameter: At apex: About 0.5 mm. At flower: About 3 mm. Aspect: Curved. Texture: Smooth, glabrous. Color: 53B to 53C.

*Peduncles.*—Length: About 5.3 cm. Diameter: About 2 mm. Texture: Smooth, glabrous. Strength: Strong, flexible. Color: 182A.

*Reproductive organs.*—Androecium: Stamen number: Five fused at anthers, hooded; filaments free. Anther length: About 5 mm to 6 mm. Anther shape: Obovate. Anther color: 46C. Pollen amount: Moderate. Pollen color: 8D. Gynoecium: Pistil quantity: One per flower. Pistil length: About 5 mm to 6 mm. Stigma color: 158A. Style color: 158A. Ovary: Five-celled. Ovary color: 137A; with development, 147A.

*Seed/fruit.*—Seed and fruit development has not been observed.

Disease/pest resistance: Plants of the new *Impatiens* have not been observed to be resistant to pathogens and pests common to *Impatiens*.

Low temperature tolerance: Plants of the new *Impatiens* have been observed to tolerate night temperatures of 5° C. with 10° C. day temperatures.

It is claimed:

1. A new and distinct cultivar of New Guinea *Impatiens* plant named 'Fisco Deepsalm', as illustrated and described.

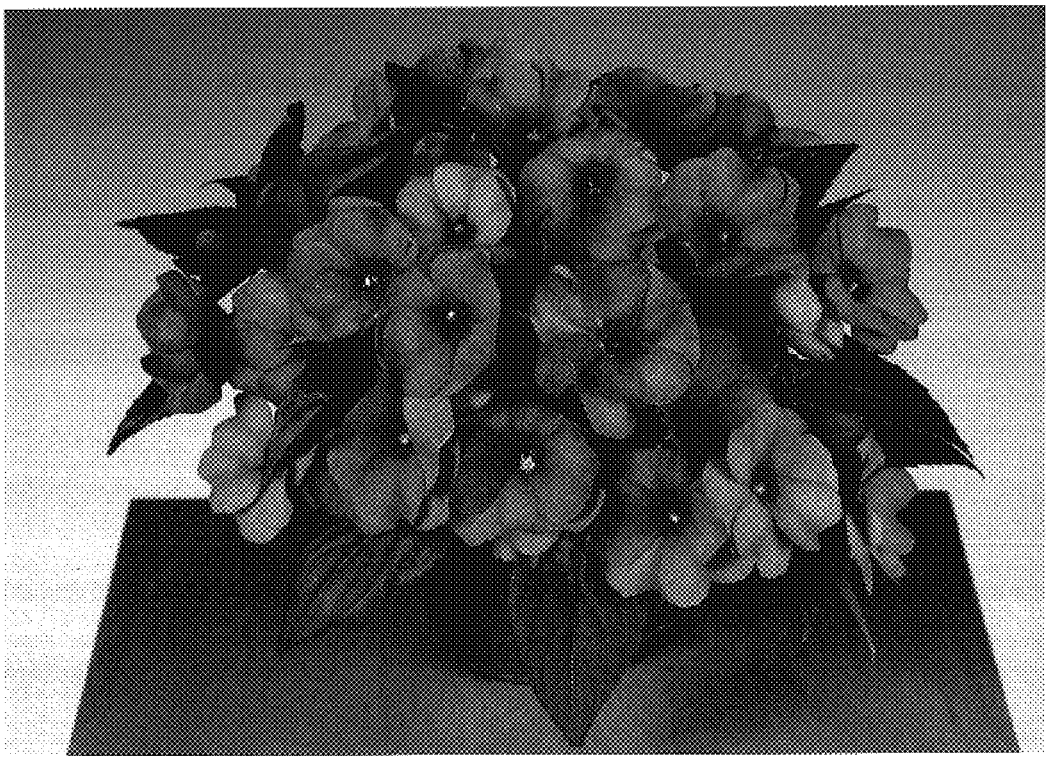

* * * * *